United States Patent
Kim et al.

(10) Patent No.: US 7,867,142 B2
(45) Date of Patent: Jan. 11, 2011

(54) METHOD AND APPARATUS FOR MANAGING EXERCISE STATE OF USER

(75) Inventors: Soo Kwan Kim, Seongnam-si (KR); Jin Sang Hwang, Suwon-si (KR); Kyung Ho Kim, Yongin-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 59 days.

(21) Appl. No.: 11/375,037

(22) Filed: Mar. 15, 2006

(65) Prior Publication Data

US 2007/0049461 A1 Mar. 1, 2007

(30) Foreign Application Priority Data

Aug. 30, 2005 (KR) .................. 10-2005-0079777

(51) Int. Cl.
*A63B 71/00* (2006.01)
(52) U.S. Cl. .............................. 482/8; 482/9; 482/900
(58) Field of Classification Search ............. 482/1, 482/3, 4, 6–9, 901, 2, 5, 900; 600/300, 301, 600/481, 500, 502; 434/236, 247, 255; 705/2; 84/612, 636, 652, 658; *A63B 71/00*
See application file for complete search history.

(56) References Cited

U.S. PATENT DOCUMENTS

| | | | | |
|---|---|---|---|---|
| 5,001,632 A * | 3/1991 | Hall-Tipping | ........... | 463/7 |
| 6,033,344 A * | 3/2000 | Trulaske et al. | ........... | 482/7 |
| 6,193,631 B1 * | 2/2001 | Hickman | ........... | 482/8 |
| 6,808,473 B2 * | 10/2004 | Hisano et al. | ........... | 482/8 |
| 7,056,265 B1 * | 6/2006 | Shea | ........... | 482/8 |
| 7,544,880 B2 * | 6/2009 | Takai et al. | ........... | 84/612 |
| 7,737,353 B2 * | 6/2010 | Sasaki et al. | ........... | 84/612 |
| 2005/0124463 A1 * | 6/2005 | Yeo et al. | ........... | 482/8 |
| 2007/0027000 A1 * | 2/2007 | Shirai et al. | ........... | 482/8 |
| 2007/0060446 A1 * | 3/2007 | Asukai et al. | ........... | 482/8 |
| 2010/0236386 A1 * | 9/2010 | Sasaki et al. | ........... | 84/612 |

FOREIGN PATENT DOCUMENTS

| | | |
|---|---|---|
| JP | 03-81999 | 8/1991 |
| JP | 10-063265 | 3/1998 |
| KR | 10-2002-0054263 | 7/2002 |
| KR | 10-2002-0066418 | 8/2002 |

(Continued)

*Primary Examiner*—Loan Thanh
*Assistant Examiner*—Oren Ginsberg
(74) *Attorney, Agent, or Firm*—Staas & Halsey LLP

(57) ABSTRACT

A method and system for providing a sound source suitable for an exercise state of a user by recognizing the exercise state of the user by measuring heart rate and exercise speed of the user. The method includes: determining a standard heart rate; measuring a heart rate of a user; measuring an exercise speed of the user; comparing the measured heart rate and the standard heart rate; when a difference between the both heart rates is more than a predetermined value, generating compensated exercise speed information based on the difference and the measured exercise speed; and replaying a sound source according to the compensated exercise speed information. According to the exercise state management method, heart rate suitable for the type, intensity, or time of exercise selected by the user and a sound source suitable for exercise speed are provided, thereby improving satisfaction and effectiveness of the exercise.

20 Claims, 4 Drawing Sheets

FOREIGN PATENT DOCUMENTS

| | | |
|---|---|---|
| KR | 10-2002-0067281 | 8/2002 |
| KR | 2003-0004513 | 1/2003 |
| KR | 2003-0070185 | 8/2003 |
| KR | 10-2004-0027017 | 4/2004 |
| KR | 10-2005-0024123 | 3/2005 |
| WO | WO 97/14357 | 4/1997 |

* cited by examiner

FIG. 2

| EXERCISE SPEED | SOUND SOURCE |
|:---:|:---:|
| V1 | M1 |
| V2 | M2 |
| ⋮ | ⋮ |

METHOD AND APPARATUS FOR MANAGING EXERCISE STATE OF USER

CROSS-REFERENCE TO RELATED APPLICATION

This application claims the benefit of Korean Patent Application No. 10-2005-79777, filed on Aug. 30, 2005, in the Korean Intellectual Property Office, the disclosure of which is incorporated herein by reference.

BACKGROUND OF THE INVENTION

1. Field of the Invention

The present invention relates to a method and an apparatus for managing an exercise state of a user, and more particularly, to a method and an apparatus for recognizing an exercise state of a user by measuring a heart rate and an exercise speed of the user and providing a sound source suitable for the exercise state of the user.

2. Description of Related Art

A representative method of recognizing an exercise state of the user is one in which a degree of exercise may be recognized by checking the heart rate of an exercising user. Generally, heart rate indicates the number of beats of a heart for one minute, and beats per minute (BPM) is used as a unit of the heart rate. The heart rate is increased when a user exercises, is mentally excited, or has a fever and is decreased when the user is at rest, is in a mentally stable state, or is asleep.

Korean Patent Laid-Open Publication No. 2005-0024123 is a representative example of a conventional method of giving feedback by recognizing an exercise state. In the conventional feedback method, a plurality of music files from a rhythm of a beat similar to a heart rate to a rhythm of a faster or slower beat, and music files having a rhythm of a predetermined beat according to heart rate of a user is included. However, since the conventional feedback method is dependant upon only the heart rate of the user, exercise speed desired by the user is not considered, thereby being difficult to keep pace with exercise speed according to an exercise state desired by the user.

On the other hand, there is Korean Patent Laid-Open Publication No. 2004-0027017 as a representative example of a conventional apparatus for replaying music files according to physical movement. The music file replay apparatus recognizes repetitive vibration of the physical movement, searches audio files having a beat corresponding to the vibration, and selects and replays an audio file having the most similar beat. However, since the conventional music file replay apparatus provides only an audio file of speed identical with present movement of a user, a sound source according to exercise speed desired by the user cannot be provided.

BRIEF SUMMARY

An aspect of the present invention provides a method and an apparatus for managing an exercise state, in which a bio signal and exercise speed of a user are measured and suitable exercise information is reported.

An aspect of the present invention also provides a method and an apparatus for managing an exercise state, in which the heart rate and exercise speed of a user are measured and an optimum exercise mode is reported to the user in real time.

An aspect of the present invention also provides a method and an apparatus for managing an exercise state, in which a heart rate measured by the exercise state management apparatus and an exercise speed of a user are considered and a sound source suitable for the user is replayed.

An aspect of the present invention also provides a method and an apparatus for managing an exercise state, in which, when a user's heart rate measured by the exercise state management apparatus is faster than a set up standard heart rate, a sound source for decreasing the heart rate speed is replayed.

An aspect of the present invention also provides a method and an apparatus for managing an exercise state, in which, when a user's heart rate measured by the exercise state management apparatus is slower than a set up standard heart rate, a sound source for increasing the heart rate is replayed.

According to an aspect of the present invention, there is provided an exercise state management method including: determining a standard heart rate; measuring a heart rate of a user; measuring an exercise speed of the user; comparing the measured heart rate and the standard heart rate to determine a difference between the rates; generating compensated exercise speed information based on the difference and the measured exercise speed, when the difference is more than a predetermined value; and replaying a sound source according to the compensated exercise speed information.

According to another aspect of the present invention, there is provided an exercise state management apparatus including: a measurement unit measuring a heart rate of a user and an exercise speed of the user; a sound source replay unit replaying a sound source; and a control unit determining standard heart rate, generating compensated exercise speed information based on the difference of the measured heart rate and the measured exercise speed, when a difference between the measured heart rate and the standard heart rate is more than a predetermined standard value, and controlling the sound source replay unit to replay a sound source corresponding to the compensated exercise speed information.

According to another aspect of the present invention, there is provided a computer-readable recording medium encoded with processing instructions for causing a processor to execute the aforementioned method.

Additional and/or other aspects and advantages of the present invention will be set forth in part in the description which follows and, in part, will be obvious from the description, or may be learned by practice of the invention.

BRIEF DESCRIPTION OF THE DRAWINGS

The above and/or other aspects and advantages of the present invention will become apparent and more readily appreciated from the following detailed description, taken in conjunction with the accompanying drawings of which:

FIG. 2 is a diagram illustrating a database storing a sound source corresponding to exercise speed in the exercise state management apparatus;

DETAILED DESCRIPTION OF EMBODIMENTS

Figure 1:
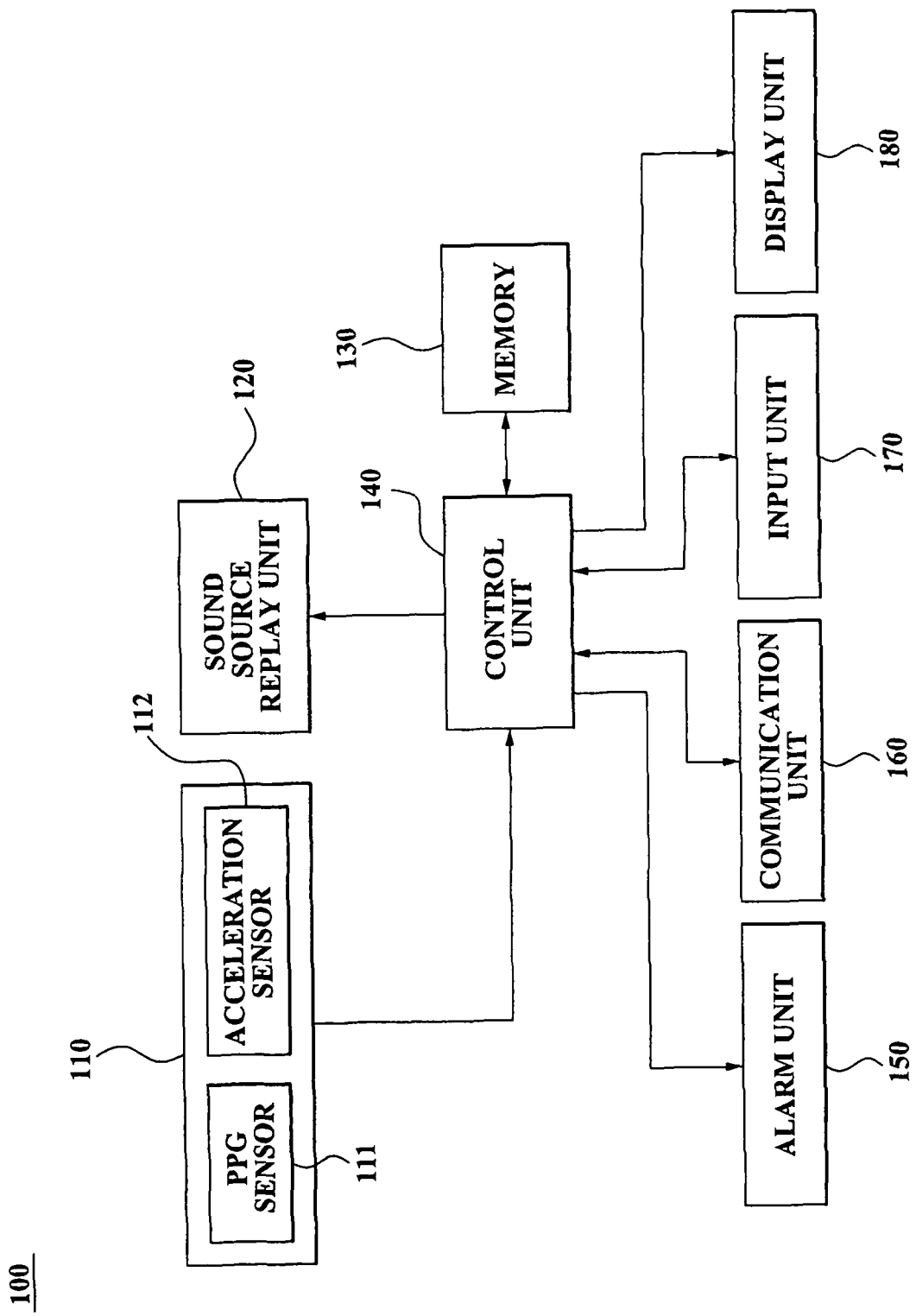
FIG. 1 is a configuration diagram illustrating an exercise state management apparatus according to an embodiment of the present invention.

Reference will now be made in detail to the embodiments of the present invention, examples of which are illustrated in the accompanying drawings, wherein like reference numerals refer to the like elements throughout. The embodiments are described below to explain the present invention by referring to the figures.

FIG. 1 is a configuration diagram illustrating an exercise state management apparatus 100 according to an embodiment of the present invention. The exercise state management apparatus 100 includes a measurement unit 110, a sound source replay unit 120, a memory 130, a control unit 140, an alarm unit 150, a communication unit 160, an input unit 170, and a display unit 180.

Referring to FIG. 1, the measurement unit 110 measures a bio signal and exercise speed of a user. The bio signal indicates a physical state of the user. For example, the bio signal may indicate heart rate of the user. The measurement unit 110 includes a photoplethysmography (PPG) sensor 111 and an acceleration sensor 112. The measurement unit 110 may measure a bio signal such as heart rate via the PPG sensor 111 attached to the surface of the skin of the user. The measurement unit 110 measures the heart rate of the user for one minute in a stable state or an exercise state of the user. The measurement unit 110 may also compute the heart rate for one minute by multiplying a heart rate value measured, for example, for 15 seconds by 4 when the heart rate is measured for 15 seconds or by multiplying a heart rate value measured for 20 seconds by 3 when the heart rate is measured for 20 seconds. The measurement unit 110 may measure exercise speed of the user via the acceleration sensor 112.

The sound source replay unit 120 replays a sound source. The sound source replay unit 120 may replay a sound source stored in a built-in sound source storage means, a sound source stored in the memory, or a sound source transmitted from a sound source providing apparatus connected via a network via the communication unit 160. The sound source replay unit 120 selects and replays a sound source corresponding to a compensated exercise speed considering the heart rate and the exercise speed of the user, from the sound sources stored in the memory according to control of the control unit 140. When a measured heart rate of the user is faster than a determined standard heart rate, the sound source replay unit 120 may select and replay a sound source having a speed corresponding to an exercise speed capable of decreasing the heart rate of the user according to the control of the control unit 140. When the measured heart rate of the user is slower than the determined standard heart rate, the sound source replay unit 120 may select and replay a sound source having a speed corresponding to exercise speed capable of increasing the heart rate of the user according to the control of the control unit 140. Accordingly, the user may adjust the exercise speed of his or herself to the speed of a sound source outputted via the sound source replay unit 120. For example, when the sound source outputted via the sound source replay unit 120 is fast dance music, the user may determine to increase a present exercise speed of his or himself and may increase the exercise speed according to the fast dance music. Also, when the sound source outputted via the sound source replay unit 120 is slow ballad music, the user may determine to decrease a present exercise speed and may decrease the exercise speed according to the slow ballad music.

The sound source replay unit 120 may replay a sound source whose speed is adjusted to be suitable for the heart rate and exercise speed of the user according to the control of the control unit 140. When the measured heart rate of the user is faster than the determined standard heart rate, the sound source replay unit 120 may control the speed of replaying the sound source to be slow and may replay the sound source in order to decrease the heart rate of the user according to the control of the control unit 140. When the measured heart rate of the user is slower than the determined standard heart rate, the sound source replay unit 120 may control the speed of replaying the sound source to be fast and may replay the sound source in order to increase the heart rate of the user according to the control of the control unit 140.

The user may control the exercise speed of his or herself to the speed of replaying the sound source outputted via the sound source replay unit 120. Namely, when the speed of replaying the sound source outputted via the sound source replay unit 120 is faster than normal speed, the user may determine that there is a need to adjust the exercise speed of his or herself to be faster and may increase the exercise speed of his or herself to the fast replay speed. Also, when the speed of replaying the sound source outputted via the sound source replay unit 120 is slower than normal speed, the user may determine that there is a need to adjust the exercise speed of his or herself to be slower and may decrease the exercise speed of his or herself to the slow replay speed.

The memory 130 stores a sound source corresponding to exercise speed. Also, the memory 130 may store exercise cool-down coefficient information.

The control unit 140 determines a standard heart rate. The standard heart rate may vary with exercise intensity, exercise type, or exercise time. The control unit 140 compares the measure heart rate of the user with the determined standard heart rate. When a difference between the measured heart rate and the determined standard heart rate is more than a predetermined standard value, the control unit 140 generates compensated exercise speed information based on the difference and the measured exercise speed.

When the measured heart rate is faster than the standard heart rate by more than the predetermined standard value, the control unit 140 generates the compensated exercise speed information lower than the measured exercise speed in order to decrease the exercise speed of the user. When the measured heart rate is faster than the standard heart rate by more than the standard value, for example, the measured exercise speed is 100 steps per minute, the control unit 140 may generate the compensated exercise speed information decreased to 90 steps per minute in order to decrease the heart rate of the user.

When the measured heart rate is slower than the standard heart rate by more than the standard value, the control unit 140 generates the compensated exercise speed information faster than the measured exercise speed in order to increase the exercise speed of the user. When the measured heart rate is slower than the standard heart rate by more than the standard value, for example, the measured exercise speed is 50 steps per minute, the control unit 140 may generate the compensated exercise speed information increased to 60 steps per minute in order to increase the heart rate of the user.

The control unit 140 controls the sound source replay unit 120 to replay a sound source corresponding to the compensated exercise speed information. The control unit 140 extracts the sound source corresponding to the compensated exercise speed information from the sound sources stored in the memory 130 and controls the sound source replay unit 120 to replay the extracted sound source. The control unit 140 extracts the sound source stored in the memory 130 and may control the sound source replay unit 120 to adjust the speed of replaying the extracted sound source to correspond to the compensated exercise speed information. The control unit 140 may store a sound source transmitted via the communication unit 160 to the memory 130, or may control the sound source replay unit 120 to directly replay the sound source transmitted via the communication unit 160 at a replay speed corresponding to the compensated exercise speed information.

The control unit 140 determines whether heart rate of the user, measured while the user exercises, is normal. When the measured heart rate of the user changes irregularly, such as suddenly increasing or decreasing, the control unit may determine the heart rate is not normal. When the heart rate of the user is determined to be not normal, the control unit 140 controls the alarm unit 150 to provide an alarm notifying the abnormality of the heart rate.

The alarm unit 150 provides a visual alarm, an audible alarm, or an electric alarm according to the control of the control unit 140. When the control unit 140 determines that the heart rate of the user is not normal, the alarm unit 150 may provide an alarm with respect to the abnormality of the heart rate. The alarm unit 150 may provide various visual alarm messages such as a text message or an icon via a graphic to the user as the visual alarm. The alarm unit 150 may provide an alarm sound or an alarm voice message notifying the abnormality of the heart rate of the user to the user as the audible alarm. The alarm unit 150 may provide the electric alarm to the user by electrically turning on an alarm means for notifying of the abnormality of the heart rate of user. The user may recognize that there is the abnormality in the heart rate of the user via the visual alarm, the audible alarm, or the electric alarm provided by the alarm unit 150 and may adjust the exercise speed.

The communication unit 160 transmits a request for a sound source desired by the user to the sound source providing apparatus connected via a network and receives a sound source transmitted from the sound source providing apparatus. The control unit 140 may control the sound source replay unit 120 to adjust replay speed of the received sound source according to the compensated exercise information.

The input unit 170 receives exercise information or self exercise evaluation information from the user. The exercise information may include age, exercise time, the exercise type, or exercise intensity of the user. The self exercise evaluation information is evaluation with respect to exercise performed by the user and may be indicated as a predetermined evaluation grade with respect to the difficulty of the exercise, for example, very hard, hard, or comfortable.

The control unit 140 may compute maximum heart rate by using the inputted age information of the user according to Equation 1:

$$\text{Maximum heart rate} = 220 - \text{age} \qquad \text{Equation (1)}.$$

When years of the user, inputted via the input unit 170 is, for example, 40, the control unit 140 may compute the maximum heart rate as "180" by Equation 1.

The control unit 140 may compute target heart rate by using the computed maximum heart rate according to Equation 2:

$$\text{Target heart rate} = \text{maximum heart rate} \times \text{percentage} \qquad \text{Equation (2)}.$$

Since the target heart rate may be computed by a certain percentage of the maximum heart rate as Equation 2, if, for example, the maximum heart rate is "180" and the percentage is "60", the control unit 140 may compute the target heart rate as "108". The control unit 140 may determine the standard heart rate by using the inputted exercise information, the computed maximum heart rate, and the computed target heart rate.

The display unit 180 displays exercise state information or exercise cool-down coefficient data of the user according to the control of the control unit 140. The control unit 140 computes the exercise cool-down coefficient by using a first heart rate measured after sustaining the exercise according to the target heart rate of the user is completed and a second heart rate measured when a determined time elapses after the sustained exercise is completed. The exercise cool-down coefficient is a difference between the first heart rate and the second heart rate and may be a basis for determining exercise ability of the user. If the exercise cool-down coefficient of the user is, for example, more than "42", the exercise ability of the user is determined to be excellent.

The display unit 180 may display the measured heart rate or exercise speed of the user according to the control of the control unit 140. The display unit 180 may display exercise evaluation information and exercise tendency information of the user according to the control of the control unit 140.

Figure 2:
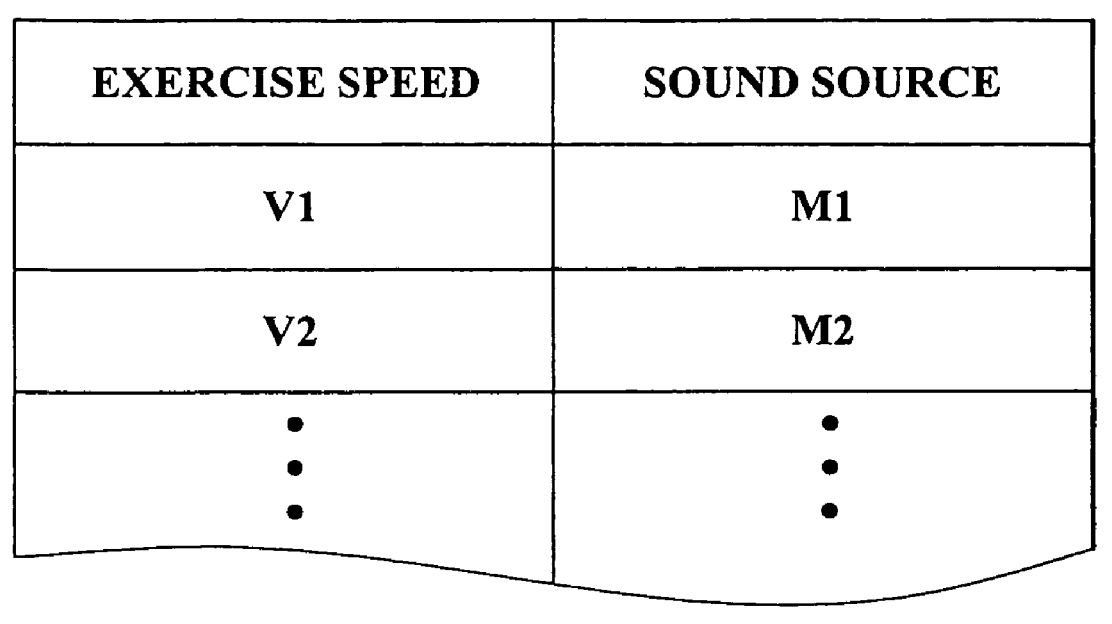

FIG. 2 is a diagram illustrating a database storing a sound source corresponding to exercise speed in the exercise state management apparatus.

Referring to FIG. 2, the exercise state management apparatus includes a sound source storage means in a memory or a sound source replay unit and constructs the database in the memory or the sound source replay unit. The database stores a sound source corresponding to exercise speed.

Figure 3:
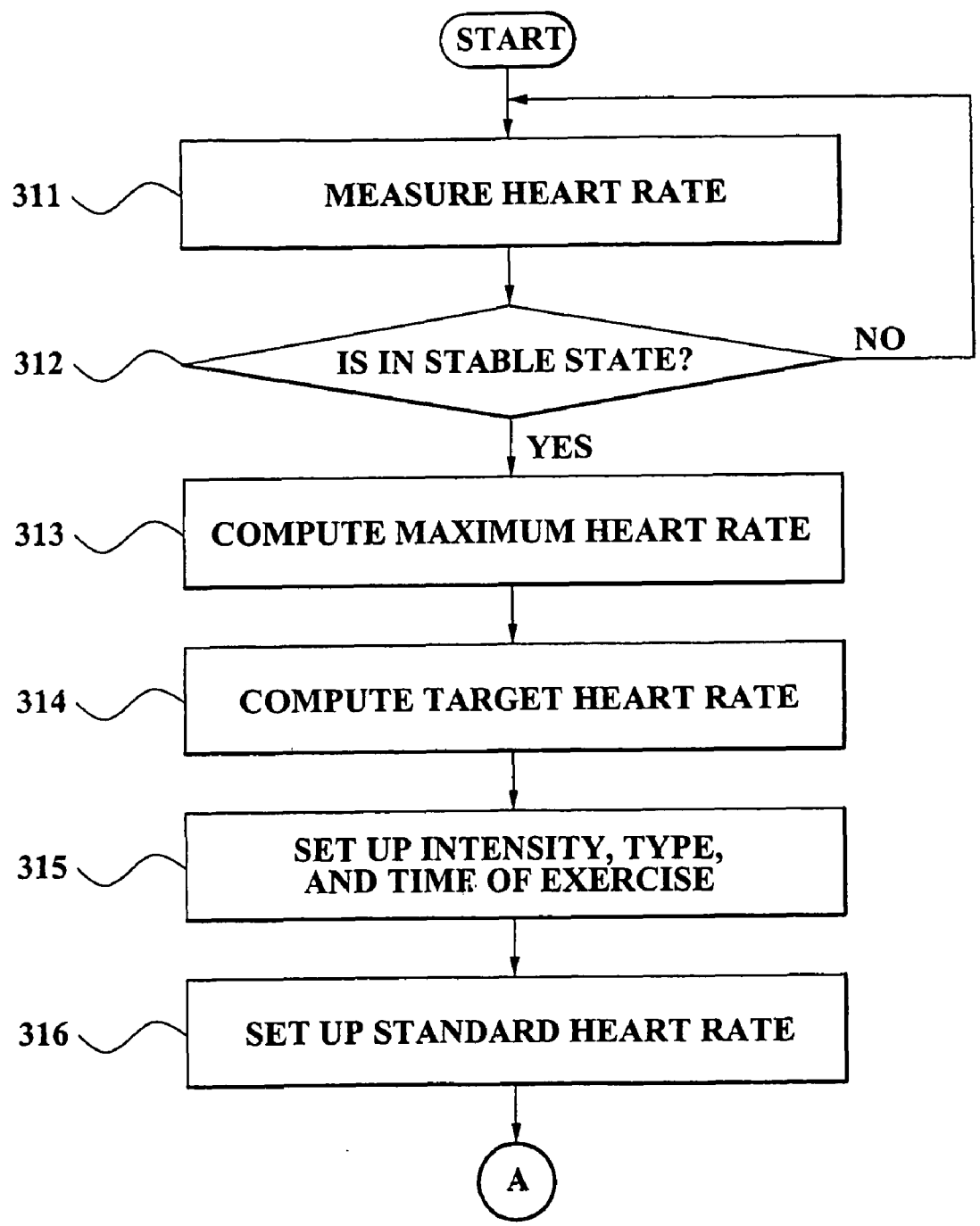
FIG. 3 is a flowchart illustrating a process of determining a standard heart rate in an exercise state management method according to an embodiment of the present invention.

FIG. 3 is a flowchart illustrating a process of determining standard heart rate in an exercise state management method according to an embodiment of the present invention.

Referring to FIG. 3, in Operation 311, an exercise state management apparatus measures heart rate of a user before the user starts exercising. The exercise state management apparatus may measure the heart rate of the user via a PPG sensor attached to the surface of the skin of the user. The PPG sensor is attached, for example, to an earlobe and may measure the heart rate of the user for a certain time. The exercise state management apparatus may measure the heart rate of the user for one minute via the PPG sensor. The exercise state management apparatus may also measure the heart rate of the user for 15 or 20 seconds via the PPG sensor and may compute the heart rate of one minute by multiplying the measured heart rate by a predetermined value. Namely, when the heart rate is measured for 15 seconds, the exercise state management apparatus may compute the heart rate of one minute by multiplying the heart rate of 15 seconds by 4. When the heart rate is measured for 20 seconds, the exercise state management apparatus may compute the heart rate of one minute by multiplying the heart rate of 20 seconds by 3.

In Operation 312, the exercise state management apparatus determines whether the measured heart rate of the user is in a stable state. If the heart rate measured before the user begins exercising is uniform, the exercise state management apparatus may determine that the heart rate is in the stable state. The case in which the heart rate of the user, in a stable state, is 70 will be described below.

In Operation 313, the exercise state management apparatus receives the age of the user from the user and computes a maximum heart rate by using the inputted age. When the age of the user is "40", the exercise state management apparatus may compute the maximum heart rate of the user as "180" by using, for example, Equation 1. When the user knows the maximum heart rate of his or herself, the exercise state management apparatus may receive the maximum heart rate directly from the user.

In Operation 314, the exercise state management apparatus computes a target heart rate by using the maximum heart rate. The exercise state management apparatus may compute the target heart rate by using, for example, Equation 2 which is a certain percentage of the maximum heart rate. When the maximum heart rate is, for example, "180" and 60 percent of the maximum heart rate is the target heart rate, the exercise state management apparatus may compute the target heart rate as "108".

In Operation 315, the exercise state management apparatus receives, from the user, exercise intensity, exercise type, or exercise time as exercise information with respect to an exercise that will be performed by the user, and set up the received exercise information. The exercise intensity, which is intensity of exercise performed by the user, may be divided into high, middle, and low or more subdivided grades. The exercise type may indicate the exercise type that will be performed by the user, such as fast walking and jogging. The exercise time is information about the time which the user exercises.

In Operation 316, the exercise state management apparatus sets up a standard heart rate by using the measured heart rate, the computed heart rate, and the set up exercise information. For example, when the user exercises for one hour, the exercise state management apparatus may set up an exercise warm-up standard heart rate for 15 minutes that is an exercise warm-up operation as "70-108", may set up a sustained exercise standard heart rate for 30 minutes that is a sustained exercise operation as "108", and may set up an exercise cool-down standard heart rate for 15 minutes that is an exercise cool-down operation as "108-70". Namely, the exercise state management apparatus may set up the exercise warm-up standard heart rate or the exercise cool-down standard heart rate based on the stable heart rate and the target heart rate according to the exercise information and may set up the target heart rate as the sustained exercise standard heart rate.

Figure 4:
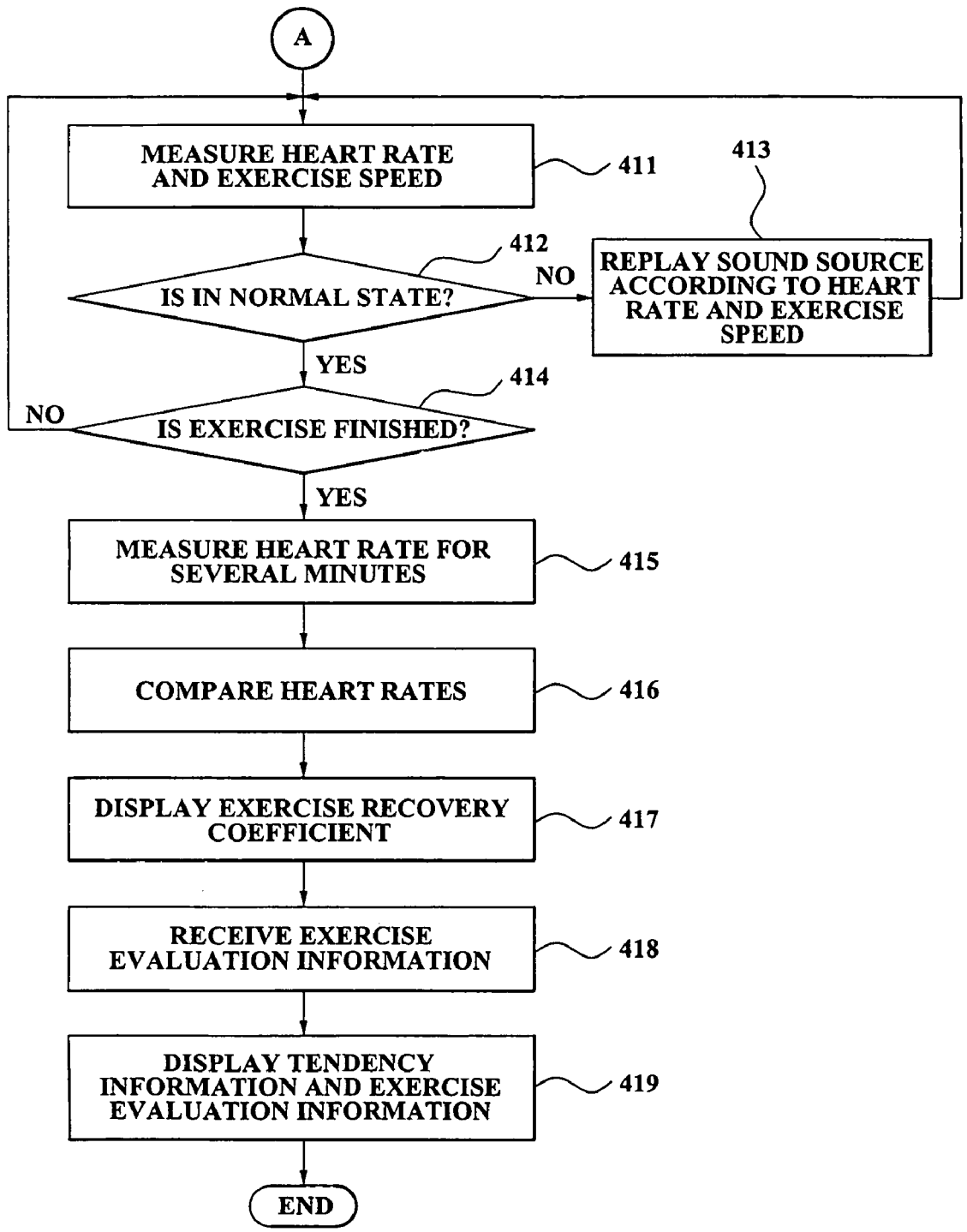
FIG. 4 is a flowchart illustrating a process of managing an exercise state by using a measured heart rate and an exercise speed in the exercise state management method.

FIG. 4 is a flowchart illustrating a process of managing an exercise state by using a measured heart rate and an exercise speed in the exercise state management method according to an embodiment of the present invention.

Referring to FIG. 4, in Operation 411, the exercise state management apparatus measures heart rate and exercise speed of a user. The user may exercise while a PPG sensor and a sound source receiver are attached to an earlobe of the user. The exercise state management apparatus measures the heart rate via the PPG sensor and may measure the exercise speed via an acceleration sensor. The exercise state management apparatus may give feedback on the measured heart rate and exercise speed to the user.

In Operation 412, the exercise state management apparatus determines whether the user is in a normal state by analyzing the measured heart rate and the exercise speed. The exercise state management apparatus compares the measured heart rate with a set up standard heart rate and, when a difference between both heart rates is more than a predetermined standard value, may determine that the heart rate of the user is abnormal.

When the heart rate of the user is abnormal, in Operation 413, the exercise state management apparatus generates compensated exercise speed information based on the difference and the measured exercise speed and replays a sound source according to the compensated exercise speed information.

When the measured heart rate is faster than the standard heart rate, the exercise state management apparatus may generate first compensated exercise speed information for decreasing the heart rate of the user. Namely, if the measured heart rate is fast, for example, the measured exercise speed of the user is 100 steps per minute, the exercise state management apparatus may generate the first compensated exercise speed information for setting up the exercise speed of the user as 90 steps per minute.

When the measured heart rate is slower than the standard heart rate, the exercise state management apparatus may generate second compensated exercise speed for increasing the heart rate of the user. Namely, if the measured heart rate is slow, for example, the measured exercise speed of the user is 50 steps per minute, the exercise state management apparatus may generate the second compensated exercise speed information for setting up the exercise speed of the user as 60 steps per minute.

The exercise state management apparatus may store and maintain sound sources corresponding to exercise speed in a memory and may extract and replay the sound source corresponding to the compensated exercise speed information from the sound sources stored in the memory.

When the heart rate of the user is abnormal, in Operation 413, the exercise state management apparatus may provide an alarm sound depending upon the severity. In this case, the abnormality of the user's heart rate may be irregular changes in the measured heart rate or a rapid increase or decrease of the user's heart rate. The exercise state management apparatus may generate an alarm message reporting a more detailed type of abnormality of the user's heart rate when the user's heart rate is abnormal. When the heart rate of the user is normal, the process returns to Operation 411.

In Operation 414, the exercise state management apparatus determines whether the user has completed exercising, via the measured heart rate or the measured exercise speed. When the user has not completed exercising, the process returns to Operation 411.

When the user has completed exercising, in Operation 415, the exercise state management apparatus measures the heart rate of the user for several minutes. The exercise state management apparatus measures a first heart rate when the user has completed exercising and measures a second heart rate when a certain time elapses after the user has completed exercising. As an example, the first heart rate may be measured at the instant the user has completed exercising, and the second heart rate may be measured at the instant when two minutes elapses after the user has completed exercising.

In Operation 416, the exercise state management apparatus compares the first heart rate with the second heart rate. The exercise state management apparatus may compute a difference between the first heart rate and the second heart rate as an exercise cool-down coefficient. The exercise state management apparatus may store the computed exercise cool-down coefficient.

In Operation 417, the exercise state management apparatus displays the computed exercise cool-down coefficient. The exercise state management apparatus may display exercise cool-down coefficient tendency information computed by using the computed exercise cool-down coefficient and a previous exercise cool-down coefficient stored when the user performed an exercise previously. When exercise cool-down coefficient, which is the difference between the first heart rate and the second heart rate, is high, exercise cool-down ability of the user is determined to be excellent.

In Operation 418, the exercise state management apparatus receives exercise evaluation information from the user. The exercise evaluation information is evaluation information on an exercise performed by the user and may be indicated as a predetermined evaluation grade with respect to the difficulty of the exercise, for example, very hard, hard, or comfortable.

In Operation 419, the exercise state management apparatus displays exercise tendency information and the exercise evaluation information of the user.

Also, embodiments of the present invention include a computer readable medium including a program instruction for executing various operations realized by a computer. The computer readable medium may include a program instruction, a data file, and a data structure, separately or cooperatively. Examples of the computer readable media include magnetic media (e.g., hard disks, floppy disks, and magnetic tapes), optical media (e.g., CD-ROMs or DVD), magneto-optical media (e.g., optical disks), and hardware devices (e.g., ROMs, RAMs, or flash memories, etc.) that are specially configured to store and perform program instructions. The media may also be transmission media such as optical or metallic lines, wave guides, etc. including a carrier wave transmitting signals specifying the program instructions, data structures, etc. Examples of the program instructions include both machine code, such as produced by a compiler, and files containing high-level languages codes that may be executed by the computer using an interpreter.

According to the above-described embodiments of the present invention, heart rate suitable for the type, intensity, or time of exercise selected by the user and a sound source suitable for exercise speed are provided, thereby improving pleasure and effectiveness of the exercise.

Also, according to the above-described embodiments of the present invention, the exercise state management apparatus may provide an optimum exercise program and exercise mode suitable for the user.

Also, according to the above-described embodiments of the present invention, the exercise state management apparatus may measure a bio signal and exercise speed of the user and may report the optimum exercise mode to the user in real time.

Also, according to the above-described embodiments of the present invention, since the exercise state management apparatus sets up a target heart rate for improving the pleasure and effectiveness when the user performs an aerobic exercise and provides a sound source having a speed similar to the exercise speed suitable for the user as background music, the user controls the exercise speed of his or herself according to speed of the background music, thereby improving exercise effectiveness.

Although a few embodiments of the present invention have been shown and described, the present invention is not limited to the described embodiments. Instead, it would be appreciated by those skilled in the art that changes may be made to these embodiments without departing from the principles and spirit of the invention, the scope of which is defined by the claims and their equivalents.

What is claimed is:

1. A computer-implemented method of managing an exercise state in an exercise state management apparatus, comprising:
    determining a standard heart rate;
    measuring a heart rate of a user;
    measuring an exercise speed of the user measured by an acceleration sensor measuring a component of the exercise state management apparatus;
    comparing the measured heart rate and the standard heart rate to determine a difference between the rates;
    generating compensated exercise speed information based on the difference and the measured exercise speed measured by the acceleration sensor, when the difference is more than a predetermined value; and
    replaying a sound source in a computer according to the compensated exercise speed information, the sound source being replayed at a speed corresponding to an exercise speed capable of increasing/decreasing the heart rate of the user, dependent on the difference between the measured and the standard heart rates.

2. The method of claim 1, wherein, in the generating compensated exercise speed information,
    when the measured heart rate is faster than the standard heart rate, first compensated exercise speed information for decreasing the heart rate of the user is generated; and
    when the measured heart rate is slower than the standard heart rate, second compensated exercise speed information for increasing the heart rate of the user is generated.

3. The method of claim 1, further comprising:
    determining whether the measured heart rate is normal; and
    generating a warning sound when the measured heart rate is not normal.

4. The method of claim 1, further comprising providing feedback to the user based on the measured heart rate and the measured exercise speed.

5. The method of claim 1, wherein, in the measuring a heart rate of the user, the heart rate of the user is measured via a photoplethysmography (PPG) sensor.

6. The method of claim 1, further comprising storing and maintaining a sound source corresponding to each exercise speed in a memory,
    wherein, in the replaying the sound source corresponding to the compensated exercise speed, the sound source corresponding to the compensated exercise speed information is extracted from the memory and replayed.

7. The method of claim 1, further comprising:
    computing an exercise cool-down coefficient of the user by using a first heart rate of the user, which is measured when the user completes an exercise, and a second heart rate of the user, which is measured when a predetermined time passes after the exercise is completed;
    displaying the computed exercise cool-down coefficient of the user;
    receiving exercise evaluation information with respect to the difficulty of the exercise performed by the user; and
    displaying the received exercise evaluation information of the user.

8. The method of claim 7, wherein the determining a standard heart rate comprises:
    measuring a stable heart rate of the user;
    receiving a maximum heart rate from the user;
    determining a target heart rate based on the received maximum heart rate;
    receiving exercise evaluation information from the user; and
    determining the standard heart rate by using the stable heart rate, the target heart rate, and the exercise information.

9. The method of claim 8, wherein the exercise evaluation information includes at least one of exercise intensity, exercise type, and exercise time information, and
    wherein the exercise evaluation information indicates a predetermined grade with respect to the difficulty of the exercise, the predetermined grade being one of very hard, hard and comfortable.

10. The method of claim 8, wherein, in the determining the standard heart rate by using the stable heart rate, the target heart rate, and the exercise evaluation information, a warm-up standard heart rate or a cool-down standard heart rate is determined based on the stable heart rate and the target heart rate according to the exercise evaluation information, and
    wherein the target heart rate is determined to be a sustained exercise standard heart rate.

11. The method of claim 7, further comprising displaying an exercise cool-down coefficient tendency computed by using the computed exercise cool-down coefficient and a previous exercise cool-down coefficient of the user, which is stored when the user performed an exercise previously.

12. A computer-executable program tangibly embodied on a computer readable medium encoded with processing instructions for causing a processor to execute a method of managing an exercise state in an exercise state management apparatus, the method comprising:
- determining a standard heart rate;
- measuring a heart rate of a user;
- measuring an exercise speed of the user measured by an acceleration sensor measuring a component of the exercise state management apparatus;
- comparing the measured heart rate and the standard heart rate to determine a difference between the rates;
- generating compensated exercise speed information based on the difference and the measured exercise speed measured by the acceleration sensor, when the difference is more than a predetermined value; and
- replaying a sound source in a computer according to the compensated exercise speed information, the sound source being replayed at a speed corresponding to an exercise speed capable of increasing/decreasing the heart rate of the user, dependent on the difference between the measured and the standard heart rates.

13. The computer-executable program of claim 12, wherein the method further comprises:
- computing an exercise cool-down coefficient of the user by using a first heart rate of the user, which is measured when the user completes an exercise, and a second heart rate of the user, which is measured when a predetermined time passes after the exercise is completed;
- displaying the computed exercise cool-down coefficient of the user;
- receiving exercise evaluation information with respect to the difficulty of the exercise performed by the user; and
- displaying the received exercise evaluation information of the user.

14. An exercise state management apparatus comprising:
- a measurement unit including a heart rate sensor measuring a heart rate of a user and an acceleration sensor measuring an exercise speed of the user by measuring a component of the exercise state management apparatus;
- a sound source replay unit replaying a sound source; and
- a control unit determining a standard heart rate and, generating compensated exercise speed information based on a difference of the measured heart rate and the measured exercise speed measured by the acceleration sensor, when the difference between the measured heart rate and a standard heart rate is more than a predetermined standard value, and controlling the sound source replay unit to replay a sound source corresponding to the compensated exercise speed information, the sound source being replayed at a speed corresponding to an exercise speed capable of increasing/decreasing the heart rate of the user, dependent on the difference between the measured and the standard heart rates.

15. The apparatus of claim 14, wherein the measurement unit further comprises a photoplethysmography (PPG) sensor measuring the heart rate of the user.

16. The apparatus of claim 14, further comprising a communication unit receiving a sound source transmitted from a sound source providing apparatus connected via a network,
- wherein the control unit controls the sound source replay unit to adjust replay speed of the received sound source according to the compensated exercise speed information.

17. The apparatus of claim 14, further comprising an alarm unit providing one of visual alarm, audible alarm, and electric alarm,
- wherein the control unit determines whether the heart rate of the user is normal by comparing with the measured heart rate and, when the heart rate of the user has an abnormality, controls the alarm unit to provide an alarm corresponding to the abnormality of the heart rate.

18. The apparatus of claim 14, further comprising an input unit receiving exercise information from the user,
- wherein the control unit determines the standard heart rate by using the exercise information received from the input unit, a computed maximum heart rate, and a target heart rate.

19. The apparatus of claim 14, wherein the controller:
- generates first compensated exercise speed information for decreasing the heart rate of the user, when the measured heart rate is faster than a standard heart rate; and
- generates second compensated exercise speed information for increasing the heart rate of the user, when the measured heart rate is slower than the standard heart rate.

20. The apparatus of claim 14, further comprising:
- an input unit receiving exercise evaluation information with respect to the difficulty of the exercise performed by the user; and
- a display unit displaying exercise condition information, exercise evaluation information and exercise cool-down coefficient data of the user,
- wherein the control unit computes the exercise cool-down coefficient data based on a first heart rate measured when the user completes an exercise and a second heart rate measured when a certain time passes after the exercise is completed and controls the display unit to display the computed exercise cool-down coefficient data and the exercise condition information.

* * * * *